United States Patent
Shi et al.

(10) Patent No.: US 7,078,486 B2
(45) Date of Patent: *Jul. 18, 2006

(54) SINGLE-CHAIN POLYPEPTIDES COMPRISING TROPONIN I AND TROPONIN C

(75) Inventors: Qinwei Shi, Etobicoke (CA); Qian-Li Song, North York (CA)

(73) Assignee: Spectral Diagnostics, Inc., Toronto (CA)

( * ) Notice: Subject to any disclaimer, the term of this patent is extended or adjusted under 35 U.S.C. 154(b) by 550 days.

This patent is subject to a terminal disclaimer.

(21) Appl. No.: 10/353,826

(22) Filed: Jan. 28, 2003

(65) Prior Publication Data

US 2003/0176655 A1 Sep. 18, 2003

Related U.S. Application Data

(63) Continuation of application No. 09/458,770, filed on Dec. 10, 1999, now abandoned.

(51) Int. Cl.
*C07K 1/00* (2006.01)
*G01N 31/10* (2006.01)

(52) U.S. Cl. ........................... 530/350; 436/15
(58) Field of Classification Search ............... 530/350; 436/15
See application file for complete search history.

(56) References Cited

U.S. PATENT DOCUMENTS

| | | | |
|---|---|---|---|
| 4,946,778 A | 8/1990 | Ladner et al. | |
| 5,290,678 A | 3/1994 | Jackowski | |
| 5,516,636 A | 5/1996 | McCapra | |
| 5,583,200 A | 12/1996 | Larue et al. | |
| 5,604,105 A | 2/1997 | Jackowski | |
| 5,696,237 A | 12/1997 | FitzGerald et al. | |
| 5,834,210 A | 11/1998 | Liu et al. | |
| 6,077,676 A * | 6/2000 | Shi et al. | 435/7.1 |
| 6,248,869 B1 | 6/2001 | Morjana et al. | |
| 6,268,481 B1 | 7/2001 | Morjana | |
| 6,475,785 B1 * | 11/2002 | Shi et al. | 435/325 |

FOREIGN PATENT DOCUMENTS

| | | |
|---|---|---|
| WO | WO 94/02610 | 2/1994 |
| WO | WO 94/27156 | 11/1994 |
| WO | WO 96/27661 | 9/1996 |
| WO | WO 97/19955 | 6/1997 |
| WO | WO 97/26534 | 7/1997 |
| WO | WO 97/39132 | 12/1997 |
| WO | WO 98/16255 | 4/1998 |
| WO | WO 98/54218 | 12/1998 |
| WO | WO 98/54219 | 12/1998 |
| WO | WO 99/31235 | 6/1999 |

OTHER PUBLICATIONS

Fujita-Baker et al., 1993, J Biochem, 114:438-44.
Hu et al., 1996, Protein Expression and Purification, 7:289-93.
Jha et al., 1996, Biochemistry, 35:11026-35.
Kobayashi et al., 1996, Biochem Biophys Acta, 124: 25-30.
Kobayashi et al., 1995, Biochemistry, 34:10946-52.
Lindbladh et al., 1994, Biochemistry, 33:11692-8.
Malnic and Reinach, 1994, Eur J Biochem, 222:49-54.
Mair et al., 1995, Clin Chem, 41:1266-72.
Vallins et al., 1990, FEBS Letters, 270:57-61.
Armour et al., 1993. Gene, 131:287-92.
Chong et al., 1981, J Biol Chem, 256:5071-6.
Kleerekoper et al., 1995, Biochemistry, 34:13343-52.
Krudy et al., 1994, J Biol Chem, 269:23731-5.
Watanapermpool, et al., 1995, Am J Physiol, 268:c323-30.
Zhang et al., 1999, Clinical Chemistry, vol. 45, No. 6, Supplement, p. A53-A54.

* cited by examiner

*Primary Examiner*—Robert A. Wax
*Assistant Examiner*—Gargi Roy
(74) *Attorney, Agent, or Firm*—Klauber & Jackson

(57) ABSTRACT

This invention relates to single-chain polypeptides and their genetic sequences comprising human cardiac troponin I and troponin C. The single-chain polypeptide may be expressed recombinantly, and a linker peptide may be interposed between the troponin sequences. A linker peptide of about 6 to about 30 amino acids is preferred. The single-chain polypeptide has utility as a control or calibrator for troponin assays, for the purification of troponin subunits and as an antigen for the preparation of antibodies.

5 Claims, 6 Drawing Sheets

FIG.1A

```
ATG GCC GAC GGT TCC AGC GAT GCG GCT AGG GAA CCT CGC CCT GCA CCA      48
Met Ala Asp Gly Ser Ser Asp Ala Ala Arg Glu Pro Arg Pro Ala Pro
 20                  25                  30                  35

GCC CCA ATC AGA CGC CGC TCC TCC AAC TAC CGC GCT TAT GCC ACG GAG      96
Ala Pro Ile Arg Arg Arg Ser Ser Asn Tyr Arg Ala Tyr Ala Thr Glu
             40                  45                  50

CCG CAC GCC AAG AAA AAA TCT AAG ATC TCC GCC TCG AGA AAA TTG CAG     144
Pro His Ala Lys Lys Lys Ser Lys Ile Ser Ala Ser Arg Lys Leu Gln
                 55                  60                  65

CTG AAG ACT CTG CTG CTG CAG ATT GCA AAG CAA GAG CTG GAG CGA GAG     192
Leu Lys Thr Leu Leu Leu Gln Ile Ala Lys Gln Glu Leu Glu Arg Glu
         70                  75                  80

GCG GAG GAG CGG CGC GGA GAG AAG GGG CGC GCT CTG GCT AGC ACC CGC TGC 240
Ala Glu Glu Arg Arg Gly Glu Lys Gly Arg Ala Leu Ala Ser Thr Arg Cys
 85                  90                  95

CAG CCG CTG GAG TTG GCC GGG CTG GGC TTC GCG GAG CTG CAG GAC TTG     288
Gln Pro Leu Glu Leu Ala Gly Leu Gly Phe Ala Glu Leu Gln Asp Leu
100                 105                 110                 115
```

FIG. 1B

```
TGC CGA CAG CTC CAC GCC CGT GTG GAC AAG GTG GAT GAA GAG AGA TAC    336
Cys Arg Gln Leu His Ala Arg Val Asp Lys Val Asp Glu Glu Arg Tyr
            120                 125                 130

GAC ATA GAG GCA AAA GTC ACC AAG AAC ATC ACG GAG ATT GCA GAT CTG    384
Asp Ile Glu Ala Lys Val Thr Lys Asn Ile Thr Glu Ile Ala Asp Leu
            135                 140                 145

ACT CAG AAG ATC TTT GAC CTT CGA GGC AAG TTT AAG CGG CCC ACC CTG    432
Thr Gln Lys Ile Phe Asp Leu Arg Gly Lys Phe Lys Arg Pro Thr Leu
            150                 155                 160

CGG AGA GTG AGG ATC TCT GCA GAT GCC ATG ATG CAG GCG CTG CTG GGG    480
Arg Arg Val Arg Ile Ser Ala Asp Ala Met Met Gln Ala Leu Leu Gly
            165                 170                 175

GCC CGG GCT AAG GAG TCC CTG GAC CTG CGG GCC CAC CTC AAG CAG GTG    528
Ala Arg Ala Lys Glu Ser Leu Asp Leu Arg Ala His Leu Lys Gln Val
            180                 185                 190                 195

AAG GAG GAC ACC GAG AAG GAA AAC CGG AAG GAG GTG GGA GAC TGG CGC    576
Lys Glu Asp Thr Glu Lys Glu Asn Arg Lys Glu Val Gly Asp Trp Arg
            200                 205                 210

AAG AAC ATC GAT GCA CTG AGT GGA ATG GAG GGC CGC AAG AAA AAG TTT    624
Lys Asn Ile Asp Ala Leu Ser Gly Met Glu Gly Arg Lys Lys Lys Phe
            215                 220                 225
```

FIG.1C

```
GAG AGC ACT AGT GGT GGT GGG GGT TCT GGT GGG GGT GGT TCT GGT GGC      672
Glu Ser Thr Ser Gly Gly Gly Gly Ser Gly Gly Gly Gly Ser Gly Gly
            230                 235                 240

GGT GGT TCT GCA TGC ATG GAT GAC ATC TAC AAG GCT GCG GTA GAG CAG      720
Gly Gly Ser Ala Cys Met Asp Asp Ile Tyr Lys Ala Ala Val Glu Gln
        245                 250                 255

CTG ACA GAA GAG CAG AAA AAT GAG TTC AAG GCA GCC TTC GAC ATC TTC      768
Leu Thr Glu Glu Gln Lys Asn Glu Phe Lys Ala Ala Phe Asp Ile Phe
260                 265                 270                 275

GTG CTG GGC GCT GAG GAT GGC TGC ATC AGC ACC AAG GAG CTG GGC AAG      816
Val Leu Gly Ala Glu Asp Gly Cys Ile Ser Thr Lys Glu Leu Gly Lys
                280                 285                 290

GTG ATG AGG ATG CTG GGC CAG AAC CCC ACC CCT GAG GAG CTG CAG GAG      864
Val Met Arg Met Leu Gly Gln Asn Pro Thr Pro Glu Glu Leu Gln Glu
            295                 300                 305

ATG ATC GAT GAG GTG GAC GAG GAC GGC AGC GGC ACG GTG GAC TTT GAT      912
Met Ile Asp Glu Val Asp Glu Asp Gly Ser Gly Thr Val Asp Phe Asp
        310                 315                 320
```

FIG.1D

```
GAG TTC CTG GTC ATG ATG GTT CGG TGC ATG AAG GAC GAC AGC AAA GGG     960
Glu Phe Leu Val Met Met Val Arg Cys Met Lys Asp Asp Ser Lys Gly
325                             330                 335

AAA TCT GAG GAG CTG TCT GAC CTC TTC CGC ATG TTT GAC AAA AAT        1008
Lys Ser Glu Glu Leu Ser Asp Leu Phe Arg Met Phe Asp Lys Asn
        340                 345                 350

GCT GAT GGC TAC ATC GAC CTG GAT GAG CTG AAG ATA ATG CTG CAG GCT    1056
Ala Asp Gly Tyr Ile Asp Leu Asp Glu Leu Lys Ile Met Leu Gln Ala
355                 360                 365                 370

ACA GGC GAG ACC ATC ACG GAG GAC GAC ATC GAG GAG CTC ATG AAG GAC    1104
Thr Gly Glu Thr Ile Thr Glu Asp Asp Ile Glu Glu Leu Met Lys Asp
            375                 380                 385

GGA GAC AAG AAC AAC GAC GGC CGC ATC GAC TAT GAT GAG TTC CTG GAG    1152
Gly Asp Lys Asn Asn Asp Gly Arg Ile Asp Tyr Asp Glu Phe Leu Glu
    390                 395                 400

TTC ATG AAG GGT GTG GAG TAG                                        1173
Phe Met Lys Gly Val Glu *
405                 410
```

Serum c TnI Assay Comparison

☐ Access
▨ Stratus
▨ Opus

Comparison of Immunostabilities of Different Forms of TnI

SINGLE-CHAIN POLYPEPTIDES COMPRISING TROPONIN I AND TROPONIN C

This application is a continuation of U.S. patent application Ser. No. 09/458,770, filed Dec. 10, 1999, now abandoned.

FIELD OF THE INVENTION

This invention relates to recombinantly-expressed, single-chain polypeptides comprising troponin subunits I and C and their corresponding genetic sequences.

BACKGROUND OF THE INVENTION

Early and accurate assessment of suspected acute myocardial infarction is critically dependent on the sensitive and specific detection and quantitation in blood, serum or plasma of released cardiac muscle intracellular components in order to distinguish a potentially lethal event in need of emergency measures from non-life threatening conditions such as angina and non-cardiac chest pain such as dyspepsia. Early electrocardiographic changes are neither adequately specific nor sensitive, and the medical profession has come to rely on serum biochemical markers of cardiac tissue injury for early diagnosis. Initially, the serum markers creatine kinase (CK) and specifically the cardiac CK-MB isoform were used, and subsequently myoglobin as a more sensitive early indicator of cardiac damage. More recently, cardiac troponin complex and its subunits have come to be preferred as markers of myocardial damage because of their high specificity. These tests in combination, along with other markers of skeletal muscle damage, provide a high degree of diagnostic accuracy. If performed in the emergency room, an early and accurate diagnosis of myocardial damage offers great advantage to a suspected heart attack victim.

Diagnostic tests employing cardiac markers are described, for example, in U.S. Pat. Nos. 5,604,105 and 5,290,678. These and other procedures offer the rapidity of diagnosing myocardial infarction in the emergency room setting and offer significant medical benefit for patients. Diagnostic tests in which the level of troponin subunits or complexes is measured in bodily fluids frequently utilize purified troponin subunits or complexes as antigens for the preparation of antibodies used in the assay procedure, as well as the purified subunits or complex used as controls and calibrators in performing the assays. Assay calibrators are used to prepare a series of dilutions by which a standard curve across the operating range of an assay is prepared; assay controls are used to confirm that an assay is operating properly by ensuring that the assayed value of pre-determined samples fall within an acceptable range around their labeled values. In order for the assay to be calibrated properly, the troponin controls and calibrators must remain stable and in a form which is immunodetectable by the antibody.

Troponin is a muscle protein integrally involved in the calcium-dependent regulation of muscle contraction. Troponin exists in both cardiac and skeletal muscle as a non-covalently-bound complex of three subunits, the isoforms troponin C, the calcium-binding subunit, troponin I, the inhibitory subunit, and troponin T, which locates the troponin complex on tropomyosin. In vitro under the proper conditions, the troponin subunits will spontaneously associate to form non-covalently-bound complexes, e.g., troponin I and C, and troponin I, C, and T. Differences exist between the amino acid sequences of the cardiac muscle and skeletal muscle troponin isoforms.

Upon cardiac muscle injury and necrosis, troponin leaks from heart tissue into circulation, where its sensitive detection can help diagnose a heart attack. The amino acid sequence differences between the cardiac and skeletal muscle isoforms of the troponin subunits are exploited in diagnostic tests which specifically measure the cardiac isoform of the troponin subunits and complexes. Diagnostic tests for cardiac troponin I are available.

However, troponin I is inherently of poor structural stability, and is subject to proteolytic cleavage by proteases present in biological samples. A troponin I standard prepared in a bodily fluid matrix is thus subject to conformational alteration and degradation and is unsuitable as a calibrator or control. Furthermore, the inherently more stable troponin complexes are known to dissociate on storage, and thus become susceptible to proteolytic degradation. In the instance of troponin I, it must be complexed with troponin C in order to help maintain its conformational structure and stability; however, because of the nature of the affinity of the subunits in the complex, the fraction of the troponin I present in the form of a complex is concentration dependent. This limits its utility as an assay calibrator or control. The extent of interactions between the subunits may be calculated from the dissociation constant, $K_d$ [for example, as reported in Biochemistry 33:12729 [1994]]. By calculation and experimental measurement, only a limited amount of troponin I is bound to troponin C, especially over the range that would be found in patient serum samples, and thus the levels at which calibrators and controls must be used. For example, at 50 ng/ml, the upper range of most troponin I assays, only 10% of the troponin I is bound to troponin C when the two subunits are present at a ratio of 1:1. With up to 10-fold more troponin C to troponin I, and in the presence of divalent cations, a claim (Larue et al., U.S. Pat. No. 5,583,200) to the stability of the complex in the cold was minimal, i.e., "at least one day." Maintaining higher concentrations of the complex increases the degree of association; however, after dilution to the level necessary to calibrate an assay, the subunits dissociate and become immunologically unstable. Dissociation then subjects the subunits to proteolytic attack, further reducing the utility of such calibrators and controls.

Thus, need exists for stable troponin calibrators and controls to meet the needs of the industry.

Numerous troponin preparations from both natural and recombinant sources have been described that contain troponin I together with troponin C. Malnic and Reinach (1994, Eur. J. Biochem., v. 222, pp. 49–54) produced a recombinant complex in vivo by cloning all three chicken skeletal muscle troponin subunits into one or more expression plasmids. Within the expression vector each troponin gene had its own promoter, and the proteins were expressed within the bacterium as individual troponin subunits, which subsequently formed complexes within the bacterium. Fujita-Becker et al. (1993, J. Biochem., v. 114, pp. 438–444) described the reconstitution of rabbit skeletal troponin complex from recombinant subunits expressed in *E. coli*. None of these recombinant products has been demonstrated to have adequate stability for use as a diagnostic test standard or calibrator. As mentioned above, even the complexes of troponin subunits are not stable and will not remain bound together in solution to any great extent.

As will be evident below, a principal object of the present invention is to provide a stable troponin preparation for assay and other uses which comprises troponin I and troponin C on a single polypeptide chain, prepared as a recombinant construct and expressed in a bacterial expression system as a single polypeptide. The present invention is distinct from troponin subunits and their fragments which have been chemically cross-linked for biochemical studies using methods such as carbodiimide cross-linking and photo-crosslinking chemistry, for example as those described by Jha et al. (1996, Biochemistry, vol. 35, pp. 11026–11035), Kobayashi et al. (1996, Biochem. Biophys. Acta, vol. 1294, pp. 25–30) and Kobayashi et al. (1995, Biochemistry, vol. 34, pp. 10946–10952). In these references, specific fragments of different troponin proteins were chemically cross-linked in order to investigate the conformations of the subunits and their natural interactions in troponin complexes.

Thus, there is a need for a troponin material which meets stability requirements and of ease of preparation of purification that may be used as an antigen and as controls and calibrators among troponin assays. As there is no universally-accepted control or calibrator for troponin, it is not possible to standardize the assay between laboratories or even instruments, as each particular troponin assay alone with its controls and calibrators produces results unique to that laboratory and selection of assay components. Thus, it is now impossible to provide normal and abnormal ranges that are recognized by all laboratories and physicians. These exists a need for universal calibrators and controls that can be used on all available commercial assay instruments.

It has now been discovered that a single-chain polypeptide comprising human cardiac troponin I and human cardiac troponin C is stable and has utility for the aforementioned purposes. Moreover, the product must be easily produced by the skilled artisan. This ease of production maximizes the reproducibility of the products of the invention.

SUMMARY OF THE INVENTION

It is a principal objective of the present invention to provide a single-chain polypeptide comprising troponin I and troponin C. The presence of troponin I and troponin C on the same polypeptide chain confers conformational stability and immunostability to the product. The single-chain polypeptide may preferably include a linker sequence interposed between the sequences of troponin I and troponin C. The sequence of the linker peptide is chosen so that it does not interfere with the tertiary structure of the product and therefore its aforementioned utilities. A single-chain polypeptide in which troponin I and troponin C are joined, optionally through a linker peptide, provides a stable, reproducible, and easily purified material for the development of troponin assays, an antigen for preparing troponin antibodies, as well as material for use as controls and calibrators for troponin assays.

The single-chain polypeptide of the present invention is prepared most readily by recombinant techniques, by constructing a replicatable cloning or expression vehicle such as a plasmid carrying the genetic sequence for the single-chain polypeptide, and transforming a host cell, such as E. coli, with the vehicle or plasmid, and expressing the polypeptide by the host cell. The single-chain construct preferably contains a linker peptide sequence between the troponin I and troponin C amino acid sequences, such sequence introduced by recombinant means. Certain modifications may be made in the genetic sequence of the troponin molecules, with or without changes in the consequent amino acid sequence of the polypeptide, in order to improve the expression of the polypeptide in the host cell. These changes do not alter the utility of the single-chain polypeptide for use in the aforementioned purposes.

It is another object of the present invention to provide a genetic sequence for a single-chain polypeptide comprising the genetic sequences of troponin I and troponin C. The genetic sequence may also include a linker genetic sequence interposed between the genetic sequences of troponin I and troponin C. A host cell may be transformed with the replicatable cloning or expression vehicle containing the aforementioned genetic sequence. As mentioned above, certain changes to the genetic sequence of the troponins may be made in order to facilitate expression in the host cell.

It is a further object of the present invention to provide a host cell containing a cloning or expression vehicle or plasmid carrying the genetic sequence for a single-chain polypeptide chain comprising the genetic sequences of troponin I and troponin C, and capable of expressing a single-chain polypeptide comprising troponin I and troponin C.

These and other aspects of the present invention will be better appreciated by reference to the following drawings and Detailed Description.

BRIEF DESCRIPTION OF THE DRAWINGS

FIG. 1 depicts the DNA and amino acid sequence (SEQ ID NO:3 and SEQ ID NO:4, respectively) of a single-chain polypeptide comprising troponin I and troponin C separated by a linker peptide of 19 amino acid residues. Nucleotides 1 through 630 comprise troponin I, nucleotides 631 through 687 comprise the linker peptide sequence, and nucleotides 688 through 1170 comprise that of troponin C.

DETAILED DESCRIPTION OF THE INVENTION

Figure 2:
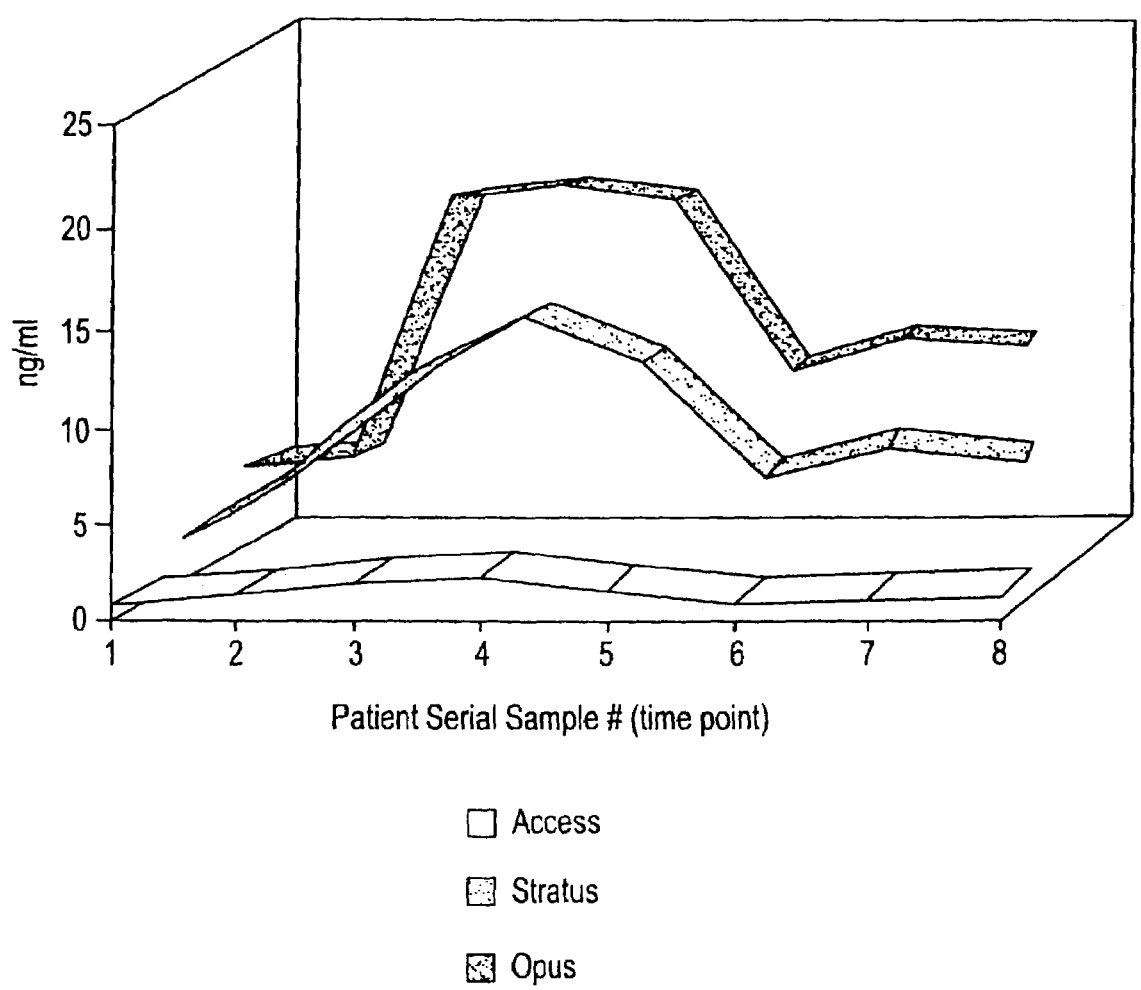
FIG. 2 depicts the results of hourly assays for troponin I from a patient undergoing a heart attack. Troponin I was measured using the Stratus(R), Access(R) and Opus(R) assays.

Measurement in circulation of the cardiac muscle-associated protein troponin has proven to be an early and specific indicator of suspected acute myocardial infarction. As such, methods for rapidly and accurately detecting troponin and its subunits in blood have been and are being developed for diagnosing heart attack in an emergency situation, and countless lives have been and will be saved as a result. However, in order to develop accurate and dependable diagnostic assays and to ensure the validity of these assays using assay controls and calibrators, the availability of stable, high-quality human cardiac troponin controls and calibrators is critical for quality control and testing purposes, as well as troponin antigens for raising antibodies for assays. Furthermore, although commercial assays for troponin have been and are being developed, these assays give different results on the same samples. The various instruments and assay methodologies for troponin in combination with the absence of a universal standard for troponin has prevented the development of widely-accepted normal and abnormal ranges for troponin levels, thus obscuring the interpretation of laboratory results and hindering inter-laboratory clinical research involving cardiac markers. These deficiencies may be remedied by the availability of universal troponin controls and calibrators. Universal controls and calibrators would be detectable by all available assays and would be used to standardize the readout provided by all troponin assays.

For utility as stable calibrators and controls for troponin assays, the present invention improves upon the inherent conformational instability and proteolytic susceptibility of free troponin I and the instability of association of the troponin I-troponin C complex. The improvement consists of a single-chain polypeptide comprising human cardiac troponin I and cardiac troponin C. The troponin subunits are thus covalently linked through a peptide bond and reside on the same linear polypeptide. This polypeptide provides a stable troponin I-troponin C complex to meet the needs of the industry. The single-chain polypeptide may be prepared by recombinant techniques, and preferably includes a linker polypeptide sequence interposed between the troponin I and troponin C sequences. The length and sequence of this linker sequence is limited only in that it does not interfere with the immunodetectability of the product and its other aforementioned utilities.

For example, one embodiment of the troponin I-troponin C single-chain polypeptide may comprise the troponin I sequence at the N-terminal portion of the polypeptide, with the C-terminus of the troponin I sequence engaged in a peptide bond with the N-terminus of the troponin C sequence. In a second and preferred embodiment wherein a linker peptide sequence is interposed between the troponin I and the troponin C amino acid sequences, one preferable arrangement comprises the troponin I sequence at the N-terminal portion of the polypeptide, its C-terminus engaged in a peptide bond with the N-terminus of the linker peptide, and the C-terminus of the linker peptide then engaged in a peptide bond with the N-terminus of the troponin C sequence. An example of this construct is the amino acid sequence depicted in SEQ ID NO:4. In this example, the amino acid sequence of the linker is represented in SEQ ID NO:2. It contains 19 amino acids.

The amino acid sequences in the above example correspond to the nucleotide sequences of the cDNA coding for these polypeptides. The genetic sequence in the first example comprises the troponin I genetic sequence at the 5' end of the cDNA, its 3' end followed immediately by the 5' end of the troponin C genetic sequence. In the preferred embodiment wherein a linker is interposed between the troponin I and troponin C sequences, the 5' of the cDNA sequence begins with the troponin I genetic sequence, its 3' end followed by the 5' end of the optional interposed linker genetic sequence, and its 3' end followed by the 5' end of the troponin C genetic sequence, ending at the 3' end of the cDNA. In the specific example above, the genetic sequence is represented in SEQ ID NO:3. The cDNA sequence of the linker is presented in SEQ ID NO:1.

As described above, selection of the length and specific sequence of the optional linker polypeptide is limited only in that it must not interfere with the immunodetectability of the troponin I and troponin C on the single-chain polypeptide. It is believed that with a suitable linker sequence, the troponin I and troponin C segments of the single polypeptide chain associate with each other in a similar fashion as they do in a non-covalent troponin I-troponin C complex, and the attachment of the subunits in the single polypeptide chain maintains the conformation of the association and thus the consistent immunodetectability of the troponin. Furthermore, a troponin I-troponin C complex stabilized in this manner is less susceptible to proteolytic attack in the presence of bodily fluids and other components. Within this preferred embodiment, a linker of about 6 to about 50 amino acids (and a corresponding number of codons in the cDNA) is preferred, for ease and economics of preparation.

It is preferred to produce the single-chain troponin I—troponin C polypeptide of this invention with a relatively short linker segment because with such products, there is little or no interference with the tertiary structure of the product. Hence there is little or no interference with the availability of epitopes for reaction with readily-available antibodies. It is known that in the usual troponin I—troponin C complex the amino terminus of the troponin I component is quite close to the carboxy terminus of the troponin C component. However, if these units form without a linker this proximity may be disturbed and the resulting strain on the tertiary structure causes some epitopes to become unavailable for reaction. In like manner, linkers which are too long may modify the tertiary structure or the linker itself may obscure some of the epitopes.

For example, a useful linker polypeptide sequence is $(Gly_4Ser)_3$ which provides a flexible peptide sequence that allows the two subunits to associate. In order to construct the genetic sequence with a linker, an additional 2 codons at each end of the linker are present, which were needed in order to provide unique restriction sites to create the genetic construct of the desired single-chain polypeptide. In one example, codons corresponding to Thr-Ser at the N-terminus of the linker and Ala-Cys at the C-terminus, may be included. Thus, a suitable 19-residue linker may be prepared (genetic sequence SEQ ID NO:1 and peptide SEQ ID NO:2).

Recombinant methods may be used to prepare the DNA sequence comprising the troponin subunits and the optional linker sequence and to introduce the sequence into a host cell, and standard expression methods are used to express and purify the recombinant polypeptide. These methods are similar to those used for the preparation of fusion proteins such as that described for the two metabolically-coupled yeast enzymes, citrate synthase and malate dehydrogenase (Lindbladh et al., Biochemistry 33:11692–11698 [1994]); in the preparation of single-chain polypeptides comprising the antigen-binding site of antibodies (U.S. Pat. No. 4,946,778); and the preparation of fusion proteins for phage display (U.S. Pat. No. 5,516,637). These methods are known to the skilled artisan.

In the instance in which no linker sequence is desired, the troponin I and troponin C cDNA sequences may be joined through suitable techniques known in the art such as the SOEing method using pairs of partially overlapping primers, for example, as described by Hu et al. (1996, Protein Expression and Purification 7:289–293) in which rare codons in human cardiac troponin T were replaced with synonymous major codons. These methods are also known to the skilled artisan.

The recombinant construct is prepared as an expression or cloning vehicle, or plasmid, and introduced into a host cell for expression. Methods for expression of recombinant proteins are known in the art. Once expressed, the single-chain polypeptide may be purified by standard protein purification methods.

Furthermore, the genetic sequences of the troponin I and troponin C may be modified in order to improve the expression of the single-chain polypeptide in a bacterial expression system. These genetic alterations may or may not alter the amino acid sequence of the polypeptide. As is known in the art, certain rare codons present in an expression vehicle reduce expression efficiency, and by changing these codons to synonymous major codons, (genetic sequence SEQ ID NO:5), bacterial expression is improved (for example, as that described for troponin I in co-pending application Ser. No. 08/862,613, filed May 23, 1997, now abandoned, and incorporated herein by reference; and methods of Hu et al., supra, also incorporated herein by reference.) In addition, the inclusion of a short nucleotide sequence to the 5' end of the troponin I cDNA (such as that described in Ser. No. 08/862,613) increases bacterial expression, and provides a troponin I polypeptide with an additional six N-terminal amino acids. (Peptide SEQ ID NO: 6) These optional modifications to increase bacterial expression do not detract from the utility of the single-chain polypeptide for the aforementioned purposes.

Several troponin I assays are commercially available, all of which operate using different formats, instruments, and assay controls and calibrators. For example the Stratus(R) troponin I assay from Dade utilizes a monoclonal capture and monoclonal detector antibody. The calibrator/control material is an N-terminal peptide from human cardiac troponin I. The operating range of the assay is 0–50 ng/ml, with a sensitivity of 0.6 ng/ml and a cut-off value of 1.5 ng/ml. The Access (R) troponin I assay from Sanofi also utilizes a monoclonal capture and monoclonal detector antibody, but its calibrator/control is a complex of native cardiac troponin I and troponin C. This assay has an operating range of 0–50 ng/ml, a sensitivity of 0.03 ng/ml, and a cut-off value of 0.1 ng/ml. The Opus(R) troponin I assay from Behring utilizes polyclonal antibodies as both capture and detector, has a range of 0–300 ng/ml. a sensitivity of 1 ng/ml and a cut-off value of 2 ng/ml.

Because of the differences in the methodology and components among the above-mentioned assays, the and calibrators/controls cannot be used interchangeably among assays. For example, the Stratus(R) calibrators/controls, which use a N-terminal peptide from cardiac troponin I, are not detectable in the Access(R) and Opus(R) assays, as the latter assays' antibodies are not directed to the same N-terminal peptide portion of troponin I used for the controls/calibrators. On the other hand, the Access(R) assay controls, which are detectable in the Access(R) assay with the highest level of sensitivity and cut-off value of all three assays, measure about four times higher in the Opus(R) assay. In contrast, the Opus(R) assay controls are detected poorly by the Stratus(R) assay. These results indicate that it is not possible to interchange assay calibrators/controls between assays, and that the values provided by the controls of one manufacturer's assay can only be used in interpreting assays run on that assay. This poor relationship is further borne out by the graph shown in FIG. 2, which depicts serial troponin I levels measured in a patient undergoing a heart attack, using the Access(R), Straus(R) and Opus(R) assays. As shown, although all three assays show a distinct rise then fall in troponin I levels between the first and sixth hours, the absolute values of troponin I at each time point are very different. These wide differences are attributed to the individuality of the assays and their calibrators/controls, as elaborated above.

A single-chain polypeptide of this invention comprising troponin I and troponin C may also be used for the purification of proteins and other substances including antibodies with an affinity for binding troponin I or troponin C. For example, the single-chain polypeptide of the present invention may be covalently bound to an insoluble matrix or polymer and situated in a chromatography column. A cell or tissue extract suspected of containing a material that binds troponin, or an antibody preparation raised against troponin, may be passed through the column, whereby it would adhere to the covalently-bound polypeptide. After washing the matrix, the adherent material may be eluted using a concentrated salt solution, a chaotropic agent, or other standard methods used in protein purification.

A single-chain polypeptide of the present invention may also be useful for the preparation of monoclonal or polyclonal anti-troponin antibodies, using standard methods of animal immunization or hybridoma preparation.

The single-chain polypeptide of the present invention comprising troponin I and troponin C has utility for the preparation of sensitive troponin assays and for the calibration of such assays. As will be seen from the following non-limiting examples, the single-chain polypeptide exhibits superior performance when compared to other troponin calibrators.

EXAMPLE 1

Expression of a Single-chain Human Cardiac Troponin I-troponin C Polypeptide in *E. coli*

Human cardiac troponin I and troponin C cDNAs were cloned by polymerase chain reaction (PCR) using primers designed from the published cardiac troponin I cDNA sequence (Vallins et al., FEBS Letters 270, 57–61 [1990]) and the troponin C sequence (GenBank AC: X07897). The C-terminus of the Troponin I cDNA was linked with the N-terminus of troponin C cDNA through a synthetic linker coding for $(Gly_4Ser)_3$ [genetic and peptide sequences of SEQ ID NO:1 and SEQ ID NO:2, respectively] with an unique restriction site engineered on each end. The single-chain troponin I-C cDNA construct was confirmed by DNA sequencing and cloned into expression vector pET21 (Novagen). *E. coli* BL21(DE3) cells, also available from Novagen, were transformed with the resulting plasmid and protein expression was verified by both SDS-PAGE and immunoassays. The single-chain polypeptide described above has a molecular weight of 43,700 Daltons. The genetic and polypeptide sequences are shown in SEQ ID NO:3 and SEQ ID NO:4, respectively.

The *E. coli* strain expressing the single-chain troponin I-troponin C polypeptide has been deposited with the American Type Culture Collection (ATCC), 10801 University Boulevard, Manassas, Va. 20110, on Dece. 18, 1997, and has ATCC number 98620.

EXAMPLE 2

Stability and Utility of the Polypeptide in the Troponin Assay

The single-chain troponin I-C described in Example 1 and a complex formed from native cardiac troponin I and troponin C, were evaluated in the Stratus(R), and Access(R) assays, following manufacturer's procedures for each assay. The results were as follows:

| Troponin preparation | Stratus(R) (ng/ml) | Access(R) (ng/ml) |
|---|---|---|
| Native cardiac troponin I - troponin C complex | 7.9 | 5 |

-continued

| Troponin preparation | Stratus(R) (ng/ml) | Access(R) (ng/ml) |
|---|---|---|
| Single-chain polypeptide comprising troponin I and troponin C of Example 1 | 8 | 3.8 |

These results show that the single-chain polypeptide comprising troponin I and troponin C gave assay results similar to that of the native cardiac troponin I-troponin C complex, in that the Stratus(R) assay gave similar higher values, and the Access(R) assay produced similar lower values.

EXAMPLE 3

Stability of the Single-chain Troponin I-C Polypeptide

The stability of three preparations containing troponin I was followed during storage at 4° C. for 7 days. The preparations were (1) recombinant troponin I prepared by standard methods; (2) a non-covalently-bound complex of recombinant troponin I and recombinant C, and (3) the single-chain polypeptide comprising troponin I and troponin C with an interposed linker peptide, as shown in SEQ ID NO:4. The non-covalently-bound complex of recombinant troponin I and recombinant troponin C was prepared by the procedure of copending and commonly-owned application Ser. No. 08/961,858, filed Oct. 31, 1997, and incorporated herein by reference. Briefly, human cardiac troponin C and a modified troponin I were expressed in *E. coli*. The troponin I was engineered as a recombinant product with six additional N-terminal amino acid residues, to increase its expression; troponin C was expressed with its native amino acid sequence. The modified troponin I in the presence of urea was combined with troponin C, $CaCl_2$ and $MgCl_2$, and shaken gently to promote the formation of troponin I-troponin C complexes.

The three preparations were stored in normal human serum. Troponin was assayed using the Dade Stratus II (R) assay.

Figure 3:
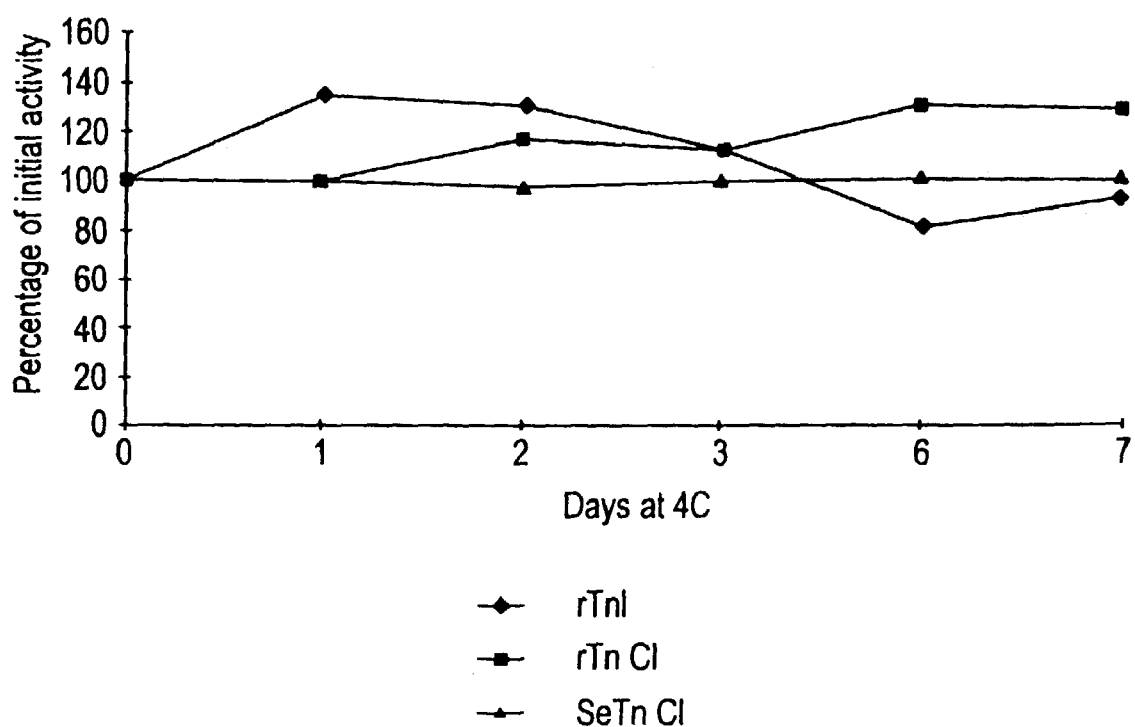
FIG. 3 depicts the stability over time at 4° C. of different preparations containing troponin I: recombinant troponin I, a non-covalent complex of troponin I and troponin C, and a single-chain polypeptide of this invention comprising troponin I and troponin C.

As shown in FIG. 3, the recombinant troponin I and the recombinant complex showed variable detectability over the 7-day period, the former first rising then falling, and the latter rising slowly over the test period. These preparations were thus unstable. In contrast, the single-chain troponin I-troponin C peptide maintained constant immunodetectability over the test period, demonstrating the stability of the material.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

Various citations to prior publications are mentioned throughout this specification, each of which is incorporated herein by reference in its entirety.

The invention claimed is:

1. A single-chain polypeptide comprising a human cardiac troponin I, a peptide linker and a human cardiac troponin C.

2. The polypeptide of claim 1 having an amino acid sequence as set forth in (SEQ ID NO: 4).

3. The single-chain polypeptide of claim 1 wherein said troponin I has sequence SEQ ID NO:6.

4. A control or calibrator composition for a troponin I assay comprising the single-chain polypeptide of claim 1.

5. A method for quantifying troponin I in a sample, the method comprising the following steps:

(1) detecting a known quantity of the single-chain polypeptide of claim 1 in a standard;

(2) detecting an unknown quantity of troponin I in a sample; and (3) correlating the unknown quantity of troponin I in the sample with the known quantity of the single-chain polypeptide on the standard.

* * * * *

SEQUENCE LISTING

<160> NUMBER OF SEQ ID NOS: 9

<210> SEQ ID NO 1
<211> LENGTH: 57
<212> TYPE: DNA
<213> ORGANISM: Artificial Sequence
<220> FEATURE:
<223> OTHER INFORMATION: synthetic

<400> SEQUENCE: 1
actagtggtg gtggtggttc tggtgggggg ggttctggtg gcggtggttc tgcatgc      57

<210> SEQ ID NO 2
<211> LENGTH: 19
<212> TYPE: PRT
<213> ORGANISM: Artificial Sequence
<220> FEATURE:
<223> OTHER INFORMATION: synthetic

<400> SEQUENCE: 2

Thr Ser Gly Gly Gly Gly Ser Gly Gly Gly Gly Ser Gly Gly Gly Gly
 1               5                  10                  15

Ser Ala Cys

<210> SEQ ID NO 3
<211> LENGTH: 1173
<212> TYPE: DNA
<213> ORGANISM: Homo sapiens

<400> SEQUENCE: 3

```
atggccgacg gttccagcga tgcggctagg gaacctcgcc ctgcaccagc cccaatcaga      60
cgccgctcct ccaactaccg cgcttatgcc acggagccgc acgccaagaa aaaatctaag     120
atctccgcct cgagaaaatt gcagctgaag actctgctgc tgcagattgc aaagcaagag     180
ctggagcgag aggcggagga gcggcgcgga gagaaggggc gcgctctgag cacccgctgc     240
cagccgctgg agttggccgg gctgggcttc gcggagctgc aggacttgtg ccgacagctc     300
cacgcccgtg tggacaaggt ggatgaagag agatacgaca tagaggcaaa agtcaccaag     360
aacatcacgg agattgcaga tctgactcag aagatctttg accttcgagg caagtttaag     420
cggcccaccc tgcggagagt gaggatctct gcagatgcca tgatgcaggc gctgctgggg     480
gcccgggcta aggagtccct ggacctgcgg gcccacctca gcaggtgaa gaaggaggac      540
accgagaagg aaaaccggga ggtgggagac tggcgcaaga acatcgatgc actgagtgga     600
atggagggcc gcaagaaaaa gtttgagagc actagtggtg gtggtggttc tggtgggggg     660
ggttctggtg gcggtggttc tgcatgcatg gatgacatct acaaggctgc ggtagagcag     720
ctgacagaag agcagaaaaa tgagttcaag gcagccttcg acatcttcgt gctgggcgct     780
gaggatggct gcatcagcac caaggagctg ggcaaggtga tgaggatgct gggccagaac     840
cccacccctg aggagctgca ggagatgatc gatgaggtgg acgaggacgg cagcggcacg     900
gtggactttg atgagttcct ggtcatgatg gttcggtgca tgaaggacga cagcaaaggg     960
aaatctgagg aggagctgtc tgacctcttc cgcatgtttg acaaaaatgc tgatggctac    1020
atcgacctgg atgagctgaa gataatgctg caggctacag gcgagaccat cacggaggac    1080
gacatcgagg agctcatgaa ggacggagac aagaacaacg acggccgcat cgactatgat    1140
gagttcctgg agttcatgaa gggtgtggag tag                                 1173
```

<210> SEQ ID NO 4
<211> LENGTH: 390
<212> TYPE: PRT
<213> ORGANISM: Homo sapiens

<400> SEQUENCE: 4

```
Met Ala Asp Gly Ser Ser Asp Ala Ala Arg Glu Pro Arg Pro Ala Pro
  1               5                  10                  15

Ala Pro Ile Arg Arg Ser Ser Asn Tyr Arg Ala Tyr Ala Thr Glu
             20                  25                  30

Pro His Ala Lys Lys Ser Lys Ile Ser Ala Ser Arg Lys Leu Gln
         35                  40                  45

Leu Lys Thr Leu Leu Leu Gln Ile Ala Lys Gln Glu Leu Glu Arg Glu
 50                  55                  60

Ala Glu Glu Arg Arg Gly Glu Lys Gly Arg Ala Leu Ser Thr Arg Cys
 65                  70                  75                  80

Gln Pro Leu Glu Leu Ala Gly Leu Gly Phe Ala Glu Leu Gln Asp Leu
                 85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
```

```
                145                 150                 155                 160
        Ala Arg Ala Lys Glu Ser Leu Asp Leu Arg Ala His Leu Lys Gln Val
                        165                 170                 175

Lys Lys Glu Asp Thr Glu Lys Glu Asn Arg Glu Val Gly Asp Trp Arg
                        180                 185                 190

Lys Asn Ile Asp Ala Leu Ser Gly Met Glu Gly Arg Lys Lys Lys Phe
                        195                 200                 205

Glu Ser Thr Ser Gly Gly Gly Ser Gly Gly Gly Ser Gly Gly
                210                 215                 220

Gly Gly Ser Ala Cys Met Asp Asp Ile Tyr Lys Ala Ala Val Glu Gln
        225                 230                 235                 240

Leu Thr Glu Glu Gln Lys Asn Glu Phe Lys Ala Ala Phe Asp Ile Phe
                        245                 250                 255

Val Leu Gly Ala Glu Asp Gly Cys Ile Ser Thr Lys Glu Leu Gly Lys
                        260                 265                 270

Val Met Arg Met Leu Gly Gln Asn Pro Thr Pro Glu Glu Leu Gln Glu
                        275                 280                 285

Met Ile Asp Glu Val Asp Glu Asp Gly Ser Gly Thr Val Asp Phe Asp
                290                 295                 300

Glu Phe Leu Val Met Met Val Arg Cys Met Lys Asp Ser Lys Gly
        305                 310                 315                 320

Lys Ser Glu Glu Glu Leu Ser Asp Leu Phe Arg Met Phe Asp Lys Asn
                        325                 330                 335

Ala Asp Gly Tyr Ile Asp Leu Asp Glu Leu Lys Ile Met Leu Gln Ala
                        340                 345                 350

Thr Gly Glu Thr Ile Thr Glu Asp Asp Ile Glu Glu Leu Met Lys Asp
                        355                 360                 365

Gly Asp Lys Asn Asn Asp Gly Arg Ile Asp Tyr Asp Glu Phe Leu Glu
                        370                 375                 380

Phe Met Lys Gly Val Glu
        385                 390

<210> SEQ ID NO 5
<211> LENGTH: 651
<212> TYPE: DNA
<213> ORGANISM: Homo sapiens

<400> SEQUENCE: 5
atggctagca tgggatctat ggcagacggt tccagcgatg cggctaggga acctcgccct      60
gcaccagccc caatcagacg ccgctcctcc aactaccgcg cttatgccac ggagccgcac     120
gccaagaaaa atctaagat ctccgcctcg agaaaattgc agctgaagac tctgctgctg     180
cagattgcaa agcaagagct ggagcgagag gcggaggagc ggcgcggaga aaggggcgc     240 gctctgagca cccgctgcca gccgctggag ttggccgggc tgggcttcgc ggagctgcag     300
gacttgtgcc gacagctcca cgcccgtgtg gacaaggtgg atgaagagag atacgacata     360
gaggcaaaag tcaccaagaa catcacggag attgcagatc tgactcagaa gatctttgac     420
cttcgaggca gtttaagcg gcccacctg cggagagtga ggatctctgc agatgccatg     480
atgcaggcgc tgctgggggc ccgggctaag gagtccctgg acctgcgggc ccacctcaag     540
caggtgaaga aggaggacac cgagaaggaa accggggagg tggagactg gcgcaagaac     600 atcgatgcac tgagtggaat ggagggccgc aagaaaaagt ttgagagctg a              651

<210> SEQ ID NO 6
```

```
<211> LENGTH: 216
<212> TYPE: PRT
<213> ORGANISM: Homo sapiens

<400> SEQUENCE: 6

Met Ala Ser Met Gly Ser Met Ala Asp Gly Ser Ser Asp Ala Ala Arg
 1               5                  10                  15

Glu Pro Arg Pro Ala Pro Ala Pro Ile Arg Arg Ser Ser Asn Tyr
            20                  25                  30

Arg Ala Tyr Ala Thr Glu Pro His Ala Lys Lys Ser Lys Ile Ser
        35                  40                  45

Ala Ser Arg Lys Leu Gln Leu Lys Thr Leu Leu Gln Ile Ala Lys
    50                  55                  60

Gln Glu Leu Glu Arg Glu Ala Glu Arg Arg Gly Glu Lys Gly Arg
65                  70                  75                  80

Ala Leu Ser Thr Arg Cys Gln Pro Leu Glu Leu Ala Gly Leu Gly Phe
                85                  90                  95

Ala Glu Leu Gln Asp Leu Cys Arg Gln Leu His Ala Arg Val Asp Lys
                100                 105                 110

Val Asp Glu Glu Arg Tyr Asp Ile Glu Ala Lys Val Thr Lys Asn Ile
                115                 120                 125

Thr Glu Ile Ala Asp Leu Thr Gln Lys Ile Phe Asp Leu Arg Gly Lys
            130                 135                 140

Phe Lys Arg Pro Thr Leu Arg Arg Val Arg Ile Ser Ala Asp Ala Met
145                 150                 155                 160

Met Gln Ala Leu Leu Gly Ala Arg Ala Lys Glu Ser Leu Asp Leu Arg
                165                 170                 175

Ala His Leu Lys Gln Val Lys Lys Glu Asp Thr Glu Lys Glu Asn Arg
                180                 185                 190

Glu Val Gly Asp Trp Arg Lys Asn Ile Asp Ala Leu Ser Gly Met Glu
            195                 200                 205

Gly Arg Lys Lys Lys Phe Glu Ser
    210                 215

<210> SEQ ID NO 7
<211> LENGTH: 15
<212> TYPE: PRT
<213> ORGANISM: Artificial Sequence
<220> FEATURE:
<223> OTHER INFORMATION: linker

<400> SEQUENCE: 7

Gly Gly Gly Gly Ser Gly Gly Gly Ser Gly Gly Gly Ser
 1               5                  10                  15

<210> SEQ ID NO 8
<211> LENGTH: 1116
<212> TYPE: DNA
<213> ORGANISM: Homo sapiens

<400> SEQUENCE: 8
atggccgacg gttccagcga tgcggctagg gaacctcgcc ctgcaccagc cccaatcaga      60
cgccgctcct ccaactaccg cgcttatgcc acggagccgc acgccaagaa aaaatctaag    120
atctccgcct cgagaaaatt gcagctgaag actctgctgc tgcagattgc aaagcaagag    180
ctggagcgag aggcggagga gcggcgcgga gagaagggc gcgctctgag cacccgctgc    240
cagccgctgg agttggccgg gctgggcttc gcggagctgc aggacttgtg ccgacagctc    300
```

```
cacgcccgtg tggacaaggt ggatgaagag agatacgaca tagaggcaaa agtcaccaag    360
aacatcacgg agattgcaga tctgactcag aagatctttg accttcgagg caagtttaag    420
cggcccaccc tgcggagagt gaggatctct gcagatgcca tgatgcaggc gctgctgggg    480
gcccgggcta aggagtccct ggacctgcgg gcccacctca gcaggtgaa gaaggaggac    540
accgagaagg aaaaccggga ggtgggagac tggcgcaaga acatcgatgc actgagtgga    600
atggagggcc gcaagaaaaa gtttgagagc atggatgaca tctacaaggc tgcggtagag    660
cagctgacag aagagcagaa aaatgagttc aaggcagcct tcgacatctt cgtgctgggc    720
gctgaggatg gctgcatcag caccaaggag ctgggcaagg tgatgaggat gctgggccag    780
aaccccaccc ctgaggagct gcaggagatg atcgatgagg tggacgagga cggcagcggc    840
acggtggact ttgatgagtt cctggtcatg atggttcggt gcatgaagga cgacagcaaa    900
gggaaatctg aggaggagct gtctgacctc ttccgcatgt ttgacaaaaa tgctgatggc    960
tacatcgacc tggatgagct gaagataatg ctgcaggcta caggcgagac catcacggag   1020
gacgacatcg aggagctcat gaaggacgga gacaagaaca acgacggccg catcgactat   1080
gatgagttcc tggagttcat gaagggtgtg gagtag                              1116
```

<210> SEQ ID NO 9
<211> LENGTH: 371
<212> TYPE: PRT
<213> ORGANISM: Homo sapiens

<400> SEQUENCE: 9

```
Met Ala Asp Gly Ser Ser Asp Ala Ala Arg Glu Pro Arg Pro Ala Pro
 1               5                  10                  15

Ala Pro Ile Arg Arg Ser Ser Asn Tyr Arg Ala Tyr Ala Thr Glu
             20                  25                  30

Pro His Ala Lys Lys Ser Lys Ile Ser Ala Ser Arg Lys Leu Gln
         35                  40                  45

Leu Lys Thr Leu Leu Leu Gln Ile Ala Lys Gln Glu Leu Glu Arg Glu
 50                  55                  60

Ala Glu Glu Arg Arg Gly Glu Lys Gly Arg Ala Leu Ser Thr Arg Cys
 65                  70                  75                  80

Gln Pro Leu Glu Leu Ala Gly Leu Gly Phe Ala Glu Leu Gln Asp Leu
             85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
            165                 170                 175

Lys Lys Glu Asp Thr Glu Lys Glu Asn Arg Glu Val Gly Asp Trp Arg
        180                 185                 190

Lys Asn Ile Asp Ala Leu Ser Gly Met Glu Gly Arg Lys Lys Phe
    195                 200                 205

Glu Ser Met Asp Asp Ile Tyr Lys Ala Ala Val Glu Gln Leu Thr Glu
210                 215                 220
```

```
Glu Gln Lys Asn Glu Phe Lys Ala Ala Phe Asp Ile Phe Val Leu Gly
225                 230                 235                 240

Ala Glu Asp Gly Cys Ile Ser Thr Lys Glu Leu Gly Lys Val Met Arg
            245                 250                 255

Met Leu Gly Gln Asn Pro Thr Pro Glu Glu Leu Gln Glu Met Ile Asp
            260             265                 270

Glu Val Asp Glu Asp Gly Ser Gly Thr Val Asp Phe Asp Glu Phe Leu
        275             280                 285

Val Met Met Val Arg Cys Met Lys Asp Asp Ser Lys Gly Lys Ser Glu
    290             295                 300

Glu Glu Leu Ser Asp Leu Phe Arg Met Phe Asp Lys Asn Ala Asp Gly
305                 310             315                 320

Tyr Ile Asp Leu Asp Glu Leu Lys Ile Met Leu Gln Ala Thr Gly Glu
            325                 330                 335

Thr Ile Thr Glu Asp Asp Ile Glu Glu Leu Met Lys Asp Gly Asp Lys
            340             345                 350

Asn Asn Asp Gly Arg Ile Asp Tyr Asp Glu Phe Leu Glu Phe Met Lys
            355             360                 365

Gly Val Glu
    370
```